United States Patent [19]  [11]  4,427,586
Numata et al.  [45]  Jan. 24, 1984

[54] 2-OXOAZETIDINE DERIVATIVES AND PRODUCTION THEREOF

[75] Inventors: Mitsuo Numata, Takatsuki; Masayoshi Yamaoka, Toyonaka; Tatsuo Nishimura, Ashiya; Norichika Matsumoto, Neyagawa, all of Japan

[73] Assignee: Takeda Chemical Industries, Ltd., Osaka, Japan

[21] Appl. No.: 321,325

[22] Filed: Nov. 13, 1981

[30] Foreign Application Priority Data

Nov. 13, 1980 [JP] Japan ..................... PCT/JP80/281

[51] Int. Cl.$^3$ ................. C07D 205/08; C07D 403/04; C07D 487/04
[52] U.S. Cl. ............................ 260/239 A; 260/245.4; 260/245.2 T
[58] Field of Search ........................ 260/239 A, 245.4

[56] References Cited

U.S. PATENT DOCUMENTS 4,262,010  4/1981  Christensen et al. ........ 260/239 AL

OTHER PUBLICATIONS

Shibuya et al., Heterocycles 12, 1315 (1979).
Oidu et al., Chem. Pharm. Bull. 28, 3494 (1980).

Primary Examiner—Mark L. Berch
Attorney, Agent, or Firm—Wenderoth, Lind & Ponack

[57] ABSTRACT

2-Oxoazetidine derivatives represented by the formula;

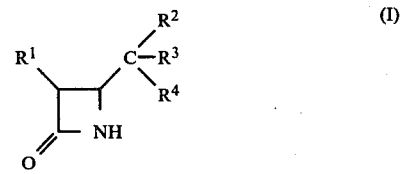

wherein $R^1$ stands for phthalimido group, benzyloxycarbonylamino group, a halogen on an alkyl group which may have hydroxyl group, $R^2$ stands for hydrogen, an alkyl group, an alkylthio group or an arylthio group, and $R^3$ and $R^4$ independently stand for an acyl group or cyano group, and a method of preparing them, which is shown by the following reaction scheme;

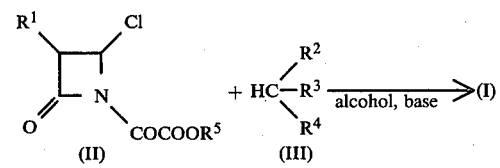

wherein $R^5$ stands for a carboxyl-protective group, and $R^1$, $R^2$, $R^3$ and $R^4$ are of the same meanings as defined above.

This compound (I) can be utilized as intermediates for carba-2-penem compounds having excellent anti-bacterial activity and $\beta$-lactamase inhibitory activity.

9 Claims, No Drawings

2-OXOAZETIDINE DERIVATIVES AND PRODUCTION THEREOF

This invention relates to novel 2-oxoazetidine derivatives, i.e., useful intermediates for the synthesis of carba-2-penem compounds having antibacterial activity or β-lactamase inhibitory activity, and production thereof. Recently a number of carba-2-penem compounds having antibiotic activity or β-lactamase inhibitory activity have aroused much attention as promising antibiotic agents, and thus development of an economical method for the preparation of these compounds in an industrial scale has become an important problem.

Since some penicillins, such as 6-aminopenicillanic acid and penicillin G are now commercially available, if the economical synthesis of carba-2-penem compounds from these penicillins could be realized, it can be a solution for the above-mentioned problem. As for a prior art concerned, a report states that a 4-chloro-2-azetidinone compound, prepared from a penicillin, is reacted with an allylcopper compound to afford an intermediate, 4-allyl-2-azetidinone compound, which is further subjected to about ten steps thereby resulting the carba-2-penem compound (Tetrahedron Letters 1979 pp. 3867–3868). In order to prepare a carba-2-penem compound from penicillin, it is, first of all, necessary to establish an advantageous method to replace the sulfur atom at the 4-position of the β-lactam ring of the penicillin with a suitable hydrocarbon residue. In this respect, the prior art was successful, taking advantage of the substitution reaction of chlorine with allylcopper compound. However, the allylcopper compounds employed in this prior art require treatment under special conditions where moisture should be strictly avoided, thus the technique disclosed in this prior art is unlikely to be practical for industrialization. Besides, the substituent which can be introduced into the 4-position of the β-lactam ring with the technique is restricted to an allyl group, which inevitably requires a number of following steps before obtaining the desired carba-2-penem compound. Thus, although, a penicillin was successfully used as the starting material, the drawbacks as mentioned above make the technique be far from being economically advantageous.

This invention relates to 2-oxoazetidine derivatives represented by the formula;

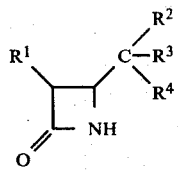

wherein $R^1$ stands for phthalimido group, benzyloxycarbonylamino group, a halogen or an alkyl group which may have hydroxyl group, $R^2$ stands for hydrogen, an alkyl group, an alkylthio group or an arylthio group, and $R^3$ and $R^4$ independently stand for an acyl group or cyano group, which are important intermediates for the synthesis of carba-2-penem-3-carboxylic acid derivatives, useful antibacterial agents, and to a method of preparing same.

The present inventors found that a compound represented by the formula (I) can be prepared by allowing a compound represented by the formula;

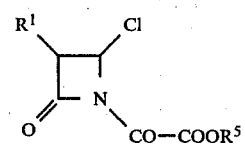

wherein $R^1$ is of the same meaning as defined above, and $R^5$ stands for a protective group of carboxyl group, to react with a compound represented by the formula;

wherein $R^2$, $R^3$ and $R^4$ are of the same meanings as defined above, respectively, in the presence of an alcohol and a base, and that various types of carba-2-penem-3-carboxylic acids can be derived from compounds represented by the formula (I) with economical advantage, thus accomplishing the present invention.

In the above formula, as the alkyl group represented by $R^1$, which may have hydroxyl group, there may be mentioned straight-chain, branched or cyclic ($C_{1-8}$) one such as methyl, ethyl, n-propyl, isopropyl, n-butyl, isobutyl, secbutyl, t-butyl, n-pentyl, isopentyl, n-hexyl, cyclopropyl, cyclobutyl, cyclopentyl or cyclohexyl, and a lower alkyl whose carbon number ranges from 1 to 6 is preferable. As especially preferable one, there may be mentioned an alkyl whose carbon number is 1 to 4. The hydroxyl group may be attached to any of the suitable positions of these alkyl groups, which are exemplified as straight-chain, branched or cyclic lower hydroxy alkyl groups whose carbon number is in the range of from 2 to 6, such as 1-hydroxyethyl, 1-hydroxyisopropyl, 2-hydroxyethyl, 1-hydroxycyclobutan-1-yl, 1-hydroxypropan-1-yl or 1-hydroxycyclohexan-1-yl. Such hydroxyl groups may be protected with e.g. acetyl, chloroacetyl, methylthiomethyl, 2,2,2-trichloroethoxycarbonyl, 1,1,1-trichloro-2-methyl-2-propoxycarbonyl, p-nitrobenzyloxycarbonyl or allyloxycarbonyl. As the halogen represented by $R^1$, there may be mentioned chlorine, bromine or iodine.

As the alkyl group represented by $R^2$, there may be mentioned straight-chain or branched ($C_{1-6}$) alkyl such as methyl, ethyl, n-propyl, isopropyl, n-butyl, sec-butyl, tert-butyl, pentyl, isopentyl, neopentyl or hexyl etc. As preferable one there may be mentioned an alkyl whose carbon number ranges 1 to 4.

As the alkylthio group represented by $R^2$, there may, for example, be mentioned a lower alkylthio group whose carbon number ranges 1 to 6, such as methylthio, ethylthio, propylthio, butylthio, pentylthio or hexylthio. As preferable one, there may be mentioned an alkylthio whose carbon number is 1 to 4 and as the arylthio group represented by $R^2$, there may for example be mentioned phenylthio or naphthylthio.

As the acyl group independently represented by $R^3$ and $R^4$, there may be mentioned $R^6$—CO— and $R^7$—CO—, respectively. The $R^6$ and $R^7$ independently stand for ($C_{1-4}$) lower alkyl e.g. methyl, ethyl, propyl or isopropyl; halogenomethyl e.g. chloromethyl or bromomethyl; methylthiomethyl; arylthiomethyl e.g. phenylthiomethyl or naphthylthiomethyl; carboxymethyl whose carboxyl may be protected; α-diazocarboxymethyl whose carboxyl may be protected; ($C_{1-4}$) lower alkoxy e.g. methoxy, ethoxy, propoxy, isopropoxy, butoxy or t-butoxy; halogeno ($C_{1-4}$) lower alkoxy e.g. 2,2,2-trichloroethoxy; aralkyloxy e.g. benzyloxy, p-nitrobenzyloxy, or o-nitrobenzyloxy; ($C_{1-4}$) lower alkylthio e.g. methylthio or ethylthio; amino ($C_{1-4}$) lower alkylthio e.g. 2-aminoethylthio whose amino group may be protected; or amino ($C_{2-4}$) lower alkenylthio e.g. 2-aminoethynylthio whose amino group may be protected.

As regards the protective groups in "the carboxyl groups which may be protected" and in the "the amino groups which may be protected," reference can be made to, for example, a known literature reference, e.g. "Protective Groups in Organic Chemistry;" Plenum Press, N.Y., 1973, compiled by J. F. W. McOmie. As the former, there may be exemplified lower alkyl e.g. methyl or 2,2,2-trichloroethyl; ($C_{4-6}$) tertiary alkyl e.g. t-butyl; ($C_{1-6}$) alkanoylmethyl e.g. acetoxymethyl or pivaloyloxymethyl; N-phthalimidomethyl; benzoylmethyl; benzyl; p-bromobenzyl; p-nitrobenzyl; p-methoxybenzyl; benzhydryl; trityl; aryl; trimethylsilyl; or triethylsilyl. As the latter, there may be exemplified monovalent protective groups e.g. t-butoxycarbonyl, trichloroethoxycarbonyl, benzyloxycarbonyl, p-methoxybenzyloxycarbonyl, p-nitrobenzyloxycarbonyl, isobornyloxycarbonyl, trityl or methyl acetoacetate adduct; or divalent protective groups e.g. phthaloyl, succinyl, maleyl or 4,5-diphenyl-4-oxazolin-2-one.

As examples of preferable one among acyl groups represented by $R^6$—CO— and $R^7$—CO—, there may be mentioned lower ($C_{1-4}$) alkylcarbonyl group, halogenoacetyl, carboxyacetyl, lower ($C_{1-4}$) alkoxycarbonylacetyl, arylthioacetyl, lower ($C_{1-4}$) alkoxycarbonyl, halogeno lower ($C_{1-4}$) alkoxycarbonyl or 2-diazo-2-(2,2,2-trichloroethoxycarbonyl)acetyl.

Selection of the protective groups to be employed is within the discretion of the artisans in the relevant technical field, and, the protective groups thus applied can, depending on cases, be removed by appropriate reaction steps.

Incidentally, free carboxyl groups of these compounds may be salts with an alkali metal such as lithium, sodium, potassium, etc., an alkali earth metal such as magnesium, calcium, barium etc., protonated ammonia, primary amine (for example methylamine, ethylamin, n-propylamine, isobutylamine, cyclohexylamin, etc.) or secondary amine (for example dimethylamine, diethylamine, diisopropylamine, dicyclohexylamine, etc.) or tertiary amine such as trimethylamine, triethylamine, tri-n-butylamine, pyridine, etc., and free amino groups may be acid addition salts with an inorganic acid such as hydrochloric acid, sulfuric acid, phosphoric acid, etc., or an organic acid such as maleic acid, acetic acid, citric acid, succinic acid, tartaric acid, malic acid, malonic acid, fumaric acid, benzoic acid, mandelic acid, ascorbic acid, methanesulfonic acid, etc.

A novel compound (I) of this invention can be prepared by, for example, allowing a 2-(4-chloro-2-oxoazetidin-1-yl)-2-oxoacetic acid derivative (II) to react with the compound (III) in the presence of an alcohol and a base. As the protective group of the carboxyl group represented by $R^5$ in the above formula (I), use can be made of, for example, those as described on $R^3$ and $R^4$.

As the alcohol in the above reaction, use can preferably be made of a ($C_{1-4}$) lower alcohol such as methanol, ethanol, propanol, isopropanol, butanol, isobutanol or t-butanol.

As the base, organic or inorganic ones can be employed, and most frequent use is made of alkali metal alcoholate e.g. lithium methoxide, sodium methoxide or potassium-t-butoxide; tertiary amine e.g. triethylamine, pyridine, dimethylaniline, diisobutylethylamine or 1,5-diazabicyclo[4,3,0]non-5-ene; alkali metal salt of secondary amine e.g. sodium hexamethyl disilazane or lithium diisopropylamine; alkali metal hydroxide e.g. sodium hydroxide; or alkali metal carbonate e.g. potassium carbonate.

The reaction is conducted in an organic solvent. As the solvent, frequent use is made of the above-mentioned alcohols, tetrahydrofuran, dioxane, diethylether, dichloromethane and a suitable mixture thereof.

The reaction can be conducted preferably in the manner described below.

Materials for the reaction are employed a 2-(4-chloro-2-oxoazetidin-1-yl)oxoacetic acid derivative represented by the formula (II), a compound represented by the formula (III), an alcohol and a base, in the equivalent ratio of 1:1–3:1–10 (when an alcohol is used as a solvent, this range may vary indefinitely): 1–3 in that order. These materials are separately or in a suitable combination dissolved in a suitable solvent or solvents. Thus the solutions are mixed together in a suitable order, whereby the reaction proceeds. The reaction temperature is preferably kept within the range from $-78°$ C. to $+5°$ C. If desired, the reaction is conducted in the streams of inert gas such as nitrogen or argon. Usually, the reaction substantially completes as soon as a compound (II), a compound (III), an alcohol and a base are all assembled but the reaction mixture may be stirred for further 0.5–5 hours.

After completion of the reaction, the object compound (I) is recovered from the reaction mixture by per se conventional manner. For example, dichloromethane and ice-water are added to the reaction mixture, and the mixture is made acidic, then the mixture is stirred vigorously, followed by separation of the dichloromethane layer. The layer is subjected to drying, followed by removal of the solvent by evaporation thereby to obtain the object compound (I).

Thus obtained object compound (I) can be purified by per se conventional process, e.g. recrystallization, column-chromatography or thin-layer chromatography.

2-Oxoazetidine compounds represented by the formula (I) are useful as intermediates for carbapenem-3-carboxylic acid derivatives useful as antibacterial agents. The compounds (I) comprise optical isomers (e.g. [3R,4R]-isomer, [3S,4S]-isomer, etc.). In these cases, the individual isomers as well as a mixture thereof fall into the scope of the present invention. The optically active compound [I] is obtained by employing an optically active compound [II] as starting material, or by optical resolution of the recemic compound [I] which may be prepared from a racemic compound [II].

2-(4-Chloro-2-oxoazetidin-1-yl)-2-oxoacetic acid derivatives (II) employed as a material in this invention can be prepared from a penicillin derivative (IV) by the reaction schema as below:

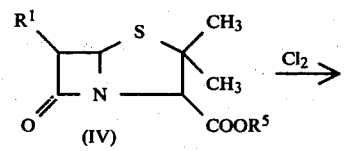

-continued

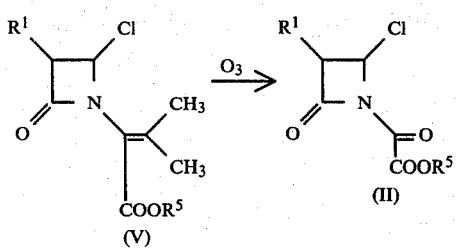

By employing the compounds of the present invention as starting materials, carba-2-penem compounds having excellent anti-bacterial activity and β-lactamase inhibitory activity (e.g. Thienamycin,—*Antimicrobial Agents and Chemotherapy*, 14, 436–438 (1978); Olivanic acid—*Journal of Antibiotics*, 33, 878–884 (1980); PS-5, —*Journal of Antibiotics*, 32, 272–279 (1979); and C-19393 H₂,—Dutch laid open patent application No. 8000-628) can be synthesized through the reaction schema as shown by the following Chart 1 and 2.

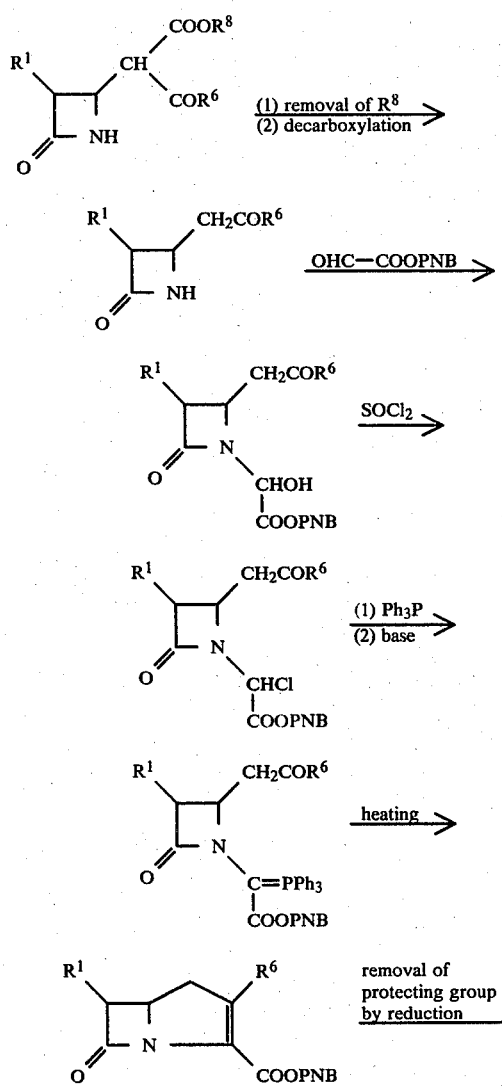

-continued
Chart 1

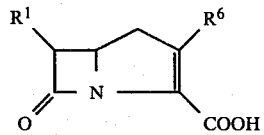

(In the formula, $R^1$ and $R^6$ are of the same meanings as defined above, $R^8$ stands for a carboxyl-protecting group, PNB stands for p-nitrobenzyl group, and Ph stands for phenyl group.)

Chart 2

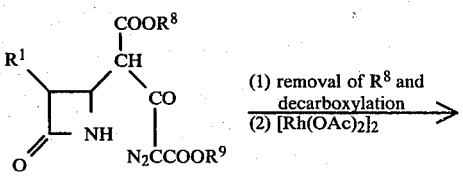

(In the formula, $R^8$ and $R^9$ respectively stand for a carboxyl-protecting group, $R^{6'}$ stands for, among those defined as $R^6$, preferably alkylthio group, 2-aminoethylthio group protected at amino group, or 2-aminoethenyl group protected at amino group, Ts stands for p-toluenesulfonyl group, and Ac stands for acetyl group.)

The present invention will be explained more concretely by way of the following Reference Examples and Examples. NMR spectra were measured by employing Varian HA 100 Type (100 MHz), EM 390 (90 MHz) or T 60 Type (60 MHz), and the values are expressed in terms of ppm, taking tetramethylsilane as the standard. The abbreviations s, br.s, d, dd, t, q, m, ABq, sh, J, DMSO, br and ar denote respectively singlet, broad singlet, doublet, double doublet, triplet, quartet, multiplet, AB type quartet, shoulder, coupling constant, dimethylsulfoxide, broad and aromatic.

In the following Reference Examples and Examples, the elution in column chromatography was carried out with observation of TLC. In the TLC, were employed Merck TLC plate 60F$_{254}$, a developing solvent which is the same as the eluent employed in the column chromatography and UV detector.

Fractions containing the desired compound, which show the same Rf value as that of main spot appearing on TLC plate at TLC for the reaction solution to be subjected to column chromatography, were collected.

The complete consumption of the starting material due to introduction of ozone was checked following the same manner as Reference Example 6.

REFERENCE EXAMPLE 1
Pivaloyloxymethyl (3R,4S)-2-[4-(chloro-3-(1-hydroxyisopropyl)-2-oxoazetidin-1-yl]-2-isopropylidenyl acetate (a) Pivaloyloxymethyl 6β-formamidopenicillanate To a mixture consisting of 113 g of pivaloyloxymethyl 6β-aminopenicillanate hydrochloride, 45 ml of triethylamine and 500 ml of dichloromethane, which is previously cooled with ice under stirring, is added dropwise a mixed anhydried of acetic acid and formic acid, which is prepared by heating a mixed solution of 30 ml of acetic anhydride and 30 ml of formic acid at 60° C. for 15 minutes, while controlling the reaction temperature not to exceed 20° C. The reaction mixture is stirred under ice-cooling for 20 minutes, which is then concentrated under reduced pressure. To the concentrate is added 500 ml of ethyl acetate. The solution is washed with water (twice with 300 ml-portion each), followed by shaking vigorously together with 500 ml of a 10% aqueous solution of sodium hydrogen carbonate. Thirty minutes later, pH of this mixture is adjusted to 7 with concentrated hydrochloric acid (ca. 30 ml), followed by separating the organic layer. The organic layer is washed with an aqueous solution of sodium chloride, then dried over magnesium sulfate, followed by concentration to leave 110 g of an oily product.

(b) Pivaloyloxymethyl 6β-carbylaminopenicillanate

A mixture consisting of 110 g of the oily product obtained in (a) above, 195 ml of pyridine and 300 ml of dichloromethane is stirred at a temperature ranging from −40° C. to −50° C., to which is added dropwise 54 ml of phosphorous oxychloride over about 2 hours, followed by stirring for further one hour at the same temperature. To the reaction mixture is added 2 kg. of crashed ice, and the mixture is stirred for about 20 minutes. The organic layer is separated, washed with an aqueous solution of sodium chloride, dried over magnesium sulfate, and concentrated to leave a syrupy product. Crystals separated out are collected by filtration with suction to yield 53 g of crystals, m.p. 96.1° C.

Elemental analysis: C$_{15}$H$_{20}$N$_2$O$_5$S

|  | C (%) | H (%) | N (%) |
|---|---|---|---|
| Calcd. | 52.93 | 5.92 | 8.23 |
| Found | 52.36 | 6.27 | 7.99 |

IR Spectrum $\nu_{max}$(CHCl$_3$): 2990, 2150, 1800, 1760, 1115 and 1000 cm$^{-1}$.

NMR spectrum (CDCl$_3$, 100 MHz) δ: 1.23(s,C(CH$_3$)$_3$), 1.54 and 1.69(each 2—C(CH$_3$)$_2$), 4.59(s,3—H), 5.22(d,J=4 Hz, 6—H), 5.56(d,J=4 Hz,5—H), 5.79 and 5.88(ABq,J=6 Hz,OCH$_2$O).

[α]$_D^{21°}$+153.2° (c=0.555, CH$_3$OH).

(c) Pivaloyloxymethyl 6α-1-hydroxyisopropyl-6β-carbylaminopenicillanate

A mixture of 11.5 g of pyvaloyloxymethyl 6β-carbylaminopenicillanate, 7 g of granular potassium carbonate and 100 ml of acetone is stirred for 7 hours under ice-cooling. The reaction mixture is subjected to filtration with suction, and the filtrate is concentrated to leave an oily substance, which is subjected to silicagel (300 g) column-chromatography by use of a mixture of n-hexane and ethyl acetate (1:1) as an eluent. Fractions containing the desired compound are collected and concentrated to leave 10 g of an oily substance, which is left standing in a refrigerator to cause crystallization, followed by loosening with n-hexane. The crystals are collected by filtration with suction. m.p. 58°–68° C.

Elemental analysis: C$_{18}$H$_{26}$N$_2$O$_6$S

|  | C (%) | H (%) | N (%) |
|---|---|---|---|
| Calcd. | 54.25 | 6.58 | 7.03 |
| Found | 54.06 | 6.80 | 7.06 |

IR Spectrum $\nu_{max}$(CHCl$_3$): 3550, 3400, 3000, 2140, 1795, 1760, 1110, 995 cm$^{-1}$.

NMR Spectrum (CDCl$_3$,100 MHz) δ: 1.23(s,C(CH$_3$)$_3$), 1.42 and 1.53(each s,(CH$_3$)$_2$CO), 1.53 and 1.66(each s,2—C—(CH$_3$)$_2$), 2.58(s,OH), 4.58(s,3—H), 5.54(s,5—H), 4.78 and 4.89(ABq,J=6 Hz, OCH$_2$O).

[α]$_D^{21°}$+149.2° (c=0.53, CH$_3$OH).

(d) Pivaloyloxymethyl 6β-1-hydroxyisopropylpenicillanate

A vessel containing a mixture of 39.8 g of pivaloyloxymethyl 6α-1-hydroxyisopropyl-6β-carbylaminopenicillanate, 41 ml of tri-n-butyltin halide, 0.82 g of α,α′-azo-bisisobutylonitrile and 200 ml of toluene is placed on an oil bath heated at 85° C., and the mixture is stirred for 30 minutes. The reaction mixture is concentrated under reduced pressure. To the concentrate is added 250 ml of n-hexane, and the mixture is stirred. Precipitating crystals are collected by filtration, and recrystallized from n-hexane-toluene to give 17.3 g of crystals, m.p. 120.3° C.

Elemental Analysis: C$_{17}$H$_{27}$NO$_6$S

|  | C (%) | H (%) |
|---|---|---|
| Calcd. | 54.67 | 7.29 |
| Found | 54.75 | 7.34 |

IR Spectrum $\nu_{max}$(CHCl$_3$): 3450, 2975, 1760, 1105, 985 cm$^{-1}$.

NMR Spectrum (CDCl$_3$, 100 MHz) δ: 1.23(s,C(CH$_3$)$_3$), 1.31, 1.44, 1.53 and 1.71(each s,2—C(CH$_3$)$_2$ and (CH$_3$)$_2$CO), 3.26(s,OH), 3.67(d,J=4.5 Hz,6—H), 4.49(s,3—H), 5.48(d,J=4.5 Hz,5—H), 5.78 and 5.88(ABq,J=6 Hz,OCH$_2$O).

[α]$_D^{20.5°}$+198.5° (c=0.595, CH$_3$OH).

(e) Pivaloyloxymethyl [3R,4S]-2-[4-chloro-3-(1-hydroxyisopropyl)-2-oxoazetidin-1-yl]-2-isopropylidenyl acetate To a solution of 18.5 g of pyvaloyloxymethyl 6β-1-hydroxyisopropylpenicillanate in 150 ml of dichloromethane which is kept at −20° C. with stirring is added dropwise 150 ml of 1 M chlorine-carbon tetrachloride solution. The mixture is stirred for 5 minutes at −20° C., then for 15 minutes at 0° C., followed by addition of 200 ml of a 10% aqueous solution of sodium hydrogen carbonate, and the mixture is stirred. The organic layer is separated, dried over magnesium sulfate and concentrated under reduced pressure to leave an oily substance, which is subjected to column chromatography packed with 300 g of silica-gel, by use of a mixture of n-hexane and ethyl acetate as an eluent. Fractions containing the desired compound are collected and concentrated to leave an oily substance. The oily substance is again subjected to column chromatography under same conditions to those above mentioned. The fractions containing the desired compound are treated with activated carbon, followed by concentration to give 14.8 g of an oily product.

Elemental analysis: $C_{17}H_{26}ClNO_6$

|  | C (%) | H (%) | N (%) | Cl (%) |
|---|---|---|---|---|
| Calcd. | 54.33 | 6.97 | 3.73 | 9.43 |
| Found | 54.11 | 7.13 | 3.62 | 10.02 |

IR Spectrum $\nu_{max}(CHCl_3)$: 3525, 2980, 1770, 1745, 1390, 1370, 1120, 990 cm$^{-1}$.

NMR Spectrum (CDCl$_3$, 100 MHz) δ: 1.24(s,C(CH$_3$)$_3$), 1.39 and 1.46(each s,(CH$_3$)$_2$CO), 2.06 and 2.33(each s,C(CH$_3$)$_2$), 2.48(s,OH), 3.47(d,J=1.6 Hz, 3—H), 5.77 and 5.87(ABq,J=6 Hz,OCH$_2$O), 5.83(d,J=1.6 Hz,4—H).

REFERENCE EXAMPLE 2

P-Nitrobenzyl [3S,4R]-2-[4-chloro-3-(1-hydroxyisopropyl)-2-oxoazetidin-1-yl]-2-isopropylidenyl acetate (a) A mixture of 27.1 g of p-nitrobenzyl 6β-aminopenicillanate p-toluenesulfonic acid salt, 250 ml of dichloromethane and 150 ml of water is stirred at a temperature ranging from −2° C. to 0° C., to which is added 4.49 g of sodium nitrite, followed by adding dropwise 50 ml of 1 N phosphoric acid over 30 minutes. The whole mixture is stirred for further 30 minutes, then the organic layer is separated. The aqueous layer is subjected to extraction with 100 ml of dichloromethane. The extract is combined with the said organic layer, which is washed with ice-water, followed by concentration under reduced pressure. The resulting oily substance is dissolved in 400 ml of acetone, which is stirred at a temperature ranging from −2° C. to 0° C. To thus cooled solution is added dropwise a mixture consisting of 60 ml of 1 N hydriodic acid and 13.4 g of sodium iodide over 30 minutes, then the whole mixture is stirred for further 30 minutes. To the reaction mixture is added 13 g of sodium hydrogen carbonate, and the mixture is stirred. The whole mixture is subjected to evaporation under reduced pressure to remove the solvent to leave an oily substance which is shaken together with 300 ml of ethyl acetate and 300 ml of water. The organic layer is separated, and washed with 200 ml of 1 N sodium thiosulfate and then with a saturated aqueous solution of sodium chloride, followed by drying on anhydrous magnesium sulfate, which is concentrated to leave an oily substance. The oil is purified by means of silica-gel column-chromatography (n-hexane-ethyl acetate=1:1 V/V). Franctions containing the desired compound are collected and concentrated to leave 9.5 g of p-nitrobenzyl 6α-iodopenicillanate as an oily product. The product is left standing overnight in a refrigerator to cause partial crystallisation, followed by loosening the crystals with acetone-dichloromethane (1:1 V/V). The crystals thus recovered are authentic specimens for analytical use. m.p. 98°–100° C.

Elemental analysis: $C_{15}H_{15}IN_2O_5S$

|  | C (%) | H (%) | N (%) |
|---|---|---|---|
| Calcd. | 38.98 | 3.27 | 6.06 |
| Found | 39.05 | 3.23 | 6.29 |

IR Spectrum $\nu_{max}$(neat); 2980, 1780, 1750, 1610, 1520, 1450, 1350, 1290 cm$^{-1}$.

NMR Spectrum (CDCl$_3$, 100 MHz) δ: 1.43 and 1.65(each s,C(CH$_3$)$_2$), 4.62(s,3—H), 5.03(d,J=1.5 Hz,5—H), 5.32(s,CH$_2$), 5.47(d,J=1.5 Hz,6—H), 7.56 and 8.26(each d,J=9 Hz, ar.H$_4$).

(b) A solution of 462 mg of p-nitrobenzyl 6α-iodopenicillanate in 5 ml of tetrahydrofuran is stirred at −73° C., to which is added 1.2 ml of 1 N methylmagnesium bromidetetrahydrofuran, followed by stirring for 10 minutes. To this mixture is added 2 ml of acetone, and the temperature of the solution is raised up to −50° C. taking 20 minutes. The temperature is again lowered to −70° C., and to the solution are added 3 ml of saturated aqueous ammonium chloride solution and 10 ml of ethyl acetate, followed by vigorous stirring. The organic layer is separated and washed with a saturated aqueous solution of sodium chloride, and dried over magnesium sulfate. The crude product obtained by removing the solvent by evaporation, is purified by means of silica-gel column chromatography (dichloromethane-ethyl acetate=(10:1)). Fractions containing the desired compound are collected and concentrated to leave 94 mg of p-nitrobenzyl 6α-1-hydroxyisopropylpenicillanate.

IR Spectrum $\nu_{max}$(KBr): 3500, 1770, 1755, 1525 cm$^{-1}$.

NMR Spectrum (CDCl$_3$, 60 MHz) δ: 1.32 and 1.60(each s,2-(C(CH$_3$)$_2$), 1.36(s,(CH$_3$)$_2$CO), 2.42(br.s,OH), 3.40(d,J=1.0 Hz,6—H), 4.59(s,3—H), 5.34(d,J=1.0 Hz,5—H), 5.34(s,CH$_2$), 7.5–8.4(m,ar.H$_4$).

(c) A solution of 98 mg of p-nitrobenzyl 6α-hydroxyisopropylpenicillanate in 2 ml of dichloromethane is stirred at −40° C., to which is added dropwise 1.65 ml of 0.45 M solution of chlorine-carbon tetrachloride. The mixture is stirred for 20 minutes at the same temperature, to which are added 10 ml of a 10% aqueous solution of sodium hydrogen carbonate and 20 ml of dichloromethane, then the whole mixture is vigorously shaken. The organic layer is separated, washed with water, then subjected to evaporation to remove the solvent. The resulting crude product is purified by means of silica-gel column chromatography (dichloromethane-ethyl acetate=10:1) to yield 39 mg of p-nitrobenzyl [3S,4R]-2-[4-chloro-3-(1-hydroxyisopropyl)-2-oxoazetidin-1-yl]-2-isopropylidenyl acetate as an oily product.

IR Spectrum $\nu_{max}$(film): 3475(br.), 1770, 1726, 1520 cm$^{-1}$.

NMR Spectrum (CDCl$_3$, 60 MHz) δ: 1.34 and 1.44(each s,(CH$_3$)$_2$CO), 1.94(br.s,OH), 2.06 and 2.32(each s,(CH$_3$)$_2$C=), 3.47(d,J=1.5 Hz,3—H), 5.30(s,CH$_2$), 5.82(d,J=1.5 Hz,4—H), 7.44–8.32(m,ar.H$_4$)

REFERENCE EXAMPLE 3

Methyl [3S,4R]-2-(4-chloro-3-phthalimido-2-oxoazetidin-1-yl)-2-isopropylidenylacetate A solution of 180 g of methyl 6α-phthalimidopenicillanate in 750 ml of dichloromethane is stirred at a temperature ranging from −55° C. to −45° C., to which is added dropwise 750 ml of 2 Mol solution of chlorine-carbon tetrachloride over about 40 minutes. Twenty minutes later, the temperature of the reaction mixture is raised up to −10° C. during one hour. The solvent is distilled off under reduced pressure.

To the residue is added 200 ml of dichloromethane, which is concentrated under reduced pressure. To the residue is again added 200 ml of dichloromethane, which is concentrated under reduced pressure. To the residue is added 200 ml of methanol, which is concentrated under reduced pressure. The residue is dissolved in 400 ml of methanol while warming, followed by left standing in a refrigerator. The precipitating crystals are collected by filtration with suction to give 140 g of the titled compound. m.p. 122°-124° C.

Elemental analysis: $C_{17}H_{15}ClN_2O_5$

|  | C (%) | H (%) | N (%) |
|---|---|---|---|
| Calcd. | 56.29 | 4.17 | 7.72 |
| Found | 55.88 | 4.10 | 7.52 |

TLC, Rf; 0.31/n-hexane-AcOEt=2:1, (Merck TLC plate 60 $F_{254}$, Germany).

IR Spectrum $\nu_{max}$(KBr): 1790, 1780, 1725, 1630, 1400 cm$^{-1}$.

NMR Spectrum (CDCl$_3$, 100 MHz) δ: 2.10 and 2.35(each s,CH$_3$)$_2$C=), 3.87(s,CH$_3$O), 5.59 and 6.25(each d,J=1.5 Hz,3—H & 4—H), 7.7-8.0(-m,ar.H$_4$).

$[\alpha]_D^{23°}$ +115.3° (c=1.13, CHCl$_3$).

REFERENCE EXAMPLE 4

Methyl [3S,4R]-2-(4-chloro-3-bromo-2-oxoazetidin-1-yl)-2-isopropylidenylacetate A solution of 14.7 g of methyl 6α-bromopenicillanate in 100 ml of dichloromethane is stirred at −50° C., to which is added dropwise 200 ml of 1 Mol solution of chlorine-carbon tetrachloride over 30 minutes. During 3 hours the temperature of the reaction mixture is raised to 10° C. The mixture is concentrated under reduced pressure. To the residue is added 30 ml of dichloromethane, which is concentrated under reduced pressure. To the residue is again added 30 ml of dichloromethane, which is concentrated under reduced pressure. The crude product thus obtained is purified by subjecting to silica-gel volumn chromatography (n-hexane-ethyl acetate=2:1) to give 14.5 g of the titled compound as an oily substance, which is left standing to cause partial crystallization, m.p. 38°-40° C.

Elemental analysis: $C_{19}H_{11}BrClNO_3$

|  | C (%) | H (%) | N (%) |
|---|---|---|---|
| Calcd. | 36.45 | 3.74 | 4.72 |
| Found | 36.13 | 3.64 | 4.99 |

IR Spectrum $\nu_{max}$(KBr): 3010, 2960, 1790, 1730, 1630, 1440, 1385, 1375 cm$^{-1}$.

NMR Spectrum (CCl$_4$, 60 MHz) δ: 2.00 and 2.33(each s,(CH$_3$)$_2$C=), 3.79(s,CH$_3$O), 4.82 and 5.78(each d,J=1 Hz,3—H and 4—H).

REFERENCE EXAMPLE 5 p-Nitrobenzyl [3S,4R]-2-(4-chloro-3-iodo-2-oxoazetidin-1-yl)-2-isopropylidenylacetate A solution of 2.31 g of p-nitrobenzyl 6α-iodopenicillanate in 15 ml of dichloromethane is stirred at a temperature ranging from −30° C. to −20° C., to which is added dropwise 30 ml of 0.9 Mol solution of chlorine-carbon tetrachloride over 30 minutes. The temperature of the mixture is allowed to rise to 0° C. during 1 hour, then the mixture is concentrated under reduced pressure. To the residue are added 30 ml of dichloromethane and 2.8 ml of triethylamine, and the mixture is stirred for 2 hours under ice-cooling. The mixture is shaken together with 70 ml of dichloromethane and 30 ml of 1 N-hydrochloric acid. The organic layer is separated, washed with a saturated aqueous solution of sodium chloride (30 ml×3), dried over magnesium sulfate, followed by concentration under reduced pressure. The resulting crude product is purified by means of silica-gel column-chromatography (dichloromethane-ethyl acetate=10:1 V/V) to give 1.264 g of the titled compound as crystals, m.p. 119°-120° C.

Elemental analysis: $C_{15}H_{14}ClIN_2O_5$

|  | C (%) | H (%) | N (%) |
|---|---|---|---|
| Calcd. | 38.78 | 3.04 | 6.03 |
| Found | 38.71 | 2.98 | 5.88 |

IR Spectrum $\nu_{max}$(neat): 3000, 1780, 1730, 1610, 1520, 1390, 1350, 1280 cm$^{-1}$.

NMR Spectrum (CDCl$_3$, 100 MHz) δ: 2.08 and 2.35(s,C(CH$_3$)$_2$), 5.23(s,CH$_2$), 5.05(d,J=1.5 Hz,4—H), 5.80(d,J=1.5 Hz,3—H),7.56 and 8.24(each d,J=9 Hz,ar.H$_4$).

$[\alpha]_D^{23°}$ +8.7° (C=1.11, CHCl$_3$).

REFERENCE EXAMPLE 6

Methyl [3S,4R]-2-(4-chloro-3-phthalimido-2-oxoazetidin-1-yl)-2-oxoacetate

A solution of 2.2 g of methyl[3S,4R]-2-(4-chloro-3-phthalimido-2-oxoazetidin-1-yl)-2-isopropylidenylacetate in 60 ml of dichloromethane is stirred at −78° C., Ozone is allowed to pass through the solution for 30 minutes (complete consumption of the starting material is observed by means of TLC (Merck TLC palte 60 F$_{254}$, developing solvent; n-hexane-AcOEt (2:1); U.V. detector), then nitrogen gas is allowed to pass through the reaction mixture for 1 hour. The reaction mixture is shaken together with 5 ml of an aqueous solution of 0.5 g of sodium hyposulfite. The organic layer is separated, washed with a saturated aqueous solution of sodium chloride dried over magnesium sulfate, and concentrated under reduced pressure. The residue is mixed with n-hexane cooled at a temperature ranging from −40° C. to −50° C. The resulting powder is collected by filtration to yield 2.1 g of the titled compound, m.p. 49°-52° C.

IR Spectrum $\nu_{max}$(KBr): 2960, 1835, 1780, 1760, 1720, 1400, 1350, 1260 cm$^{-1}$.

NMR Spectrum (CDCl$_3$, 60 MHz) δ: 4.03(s,CH$_3$), 5.73 and 6.33(each d,3—H & 4—H), 7.88(s,ar.H$_4$).

$[\alpha]_D^{21.5°}$ −34.2° (c=0.9 Dioxane).

REFERENCE EXAMPLE 7 t-Butyl 2,2,2-trichloroethyl acetonedicarboxylate

A solution of 21 g of N,N'-carbodiimidazole in 200 ml of dichloromethane is stirred under ice-cooling, to which is added dropwise a solution of 18.7 g of t-butyl malonate in 5 ml of dichloromethane, followed by stirring for 1.5 hours. This solution is added dropwise to an ice-cooled, stirred solution consisting of 16 g of Meldrum's Acid, 28 g of pyridine and 200 ml of dichloromethane over 15 minutes. The mixture is stirred for one hour under ice-cooling, then another one hour at room temperature. This mixture is shaken with 200 ml of 5 N sulfuric acid and 100 ml of water. The organic layer is washed with a saturated aqueous solution of sodium chloride, dried over magnesium sulfate, and concentrated under reduced pressure. A solution consisting of the oily residue, 41 g of 2,2,2-trichloroethanol and 300 ml of benzene is subjected to reflux for 25 minutes. The solvent is distilled off under reduced pressure, and the oily residue is dissolved in 200 ml of ethyl acetate, washed with a 10% aqueous solution of sodium carbonate and then with a saturated aqueous solution of sodium chloride, and dried over magnesium sulfate. The solvent is distilled off under reduced pressure. The oily residue is mixed with 10 ml of petroleum ether, which is left standing at a refrigerator, then crystals precipitate out. This mixture is stirred with 10 ml of cooled petroleum ether, followed by filtration with suction to yield 17 g of the titled compound as crystalline powder, m.p. 50°–52° C.

Elemental analysis: C$_{11}$H$_{15}$Cl$_3$O$_4$.H$_2$O

|  | C (%) | H (%) | Cl (%) |
| --- | --- | --- | --- |
| Calcd. | 39.37 | 5.11 | 31.69 |
| Found | 39.27 | 4.52 | 31.63 |

IR Spectrum $\nu_{max}$(KBr): 2990, 1750, 1730, 1350, 1290, 1170, 1125, 975, 815, 715 cm$^{-1}$.

NMR Spectrum (CDCl$_3$, 60 MHz) δ: 1.48(s,C(CH$_3$)$_3$), 3.60(s,CH$_2$CO$_2$t-Bu), 3.83(s,CH$_2$CO$_2$CH$_2$CCl$_3$), 4.87(s,CH$_2$CCl$_3$).

REFERENCE EXAMPLE 8

2,2,2-Trichloroethyl 2-(2-t-butoxycarbonylacetyl)-2-diazoacetate

A solution consisting of 1.6 g of t-butyl 2,2,2-trichloroethyl acetonedicarboxylate, 0.985 g of tosyl azide and 10 ml of ether is stirred under ice-cooling, to which is added dropwise 0.7 ml of triethylamine, followed by stirring for 15 minutes under ice-cooling and for 30 minutes at room temperature. The reaction mixture is mixed with 10 ml of petroleum ether, which is then stirred for 15 minutes under ice-cooling. Toluenesulfonamide precipitated is removed by filtration with suction, and the filtrate is washed with 0.5 N hydrochloride acid, dried over magnesium sulfate, followed by concentration under reduced pressure. The oily residue is dissolved in 3 ml of carbon tetrachloride, and insolubles are removed by filtration with suction. The filtrate is concentrated to dryness under reduced pressure to give 1.52 g (yield 88.5%) of the titled compound as an oily substance.

IR Spectrum $\nu_{max}$(CCl$_4$): 2990, 2150, 1730, 1670, 1370, 1330, 1140, 1050, 720 cm$^{-1}$.

NMR Spectrum (CCl$_4$, 60 MHz) δ: 1.43(s,C(CH$_3$)$_3$), 3.70(s,CH$_2$CO$_2$), 4.90(s,CH$_2$CCl$_3$).

REFERENCE EXAMPLE 9 p-Nitrobenzyl 2-ethylthiocarbonyl-2-phenylthioacetate

A solution consisting of 435 mg of p-nitrobenzyl 2-ethylthiocarbonylacetate, 377 mg of N-phenylthiosuccinimide and 5 ml of dichloromethane is stirred under ice-cooling, to which is added dropwise a solution of 0.25 ml of triethylamine in 2 ml of dichloromethane. The solution is stirred for one hour, washed with 1 N hydrochloric acid and then with a saturated aqueous solution of sodium chloride, dried over magnesium sulfate, followed by concentration to dryness under reduced pressure. The oily residue is purified by means of silica-gel column chromatography (n-hexane-ethyl acetate=3:7), and the fractions containing the desired product are collected and concentrated to dryness to yield 504 mg (yield 84%) of the titled compound as an oily substance.

IR Spectrum $\nu_{max}$(neat): 1750, 1675, 1610, 1520 cm$^{-1}$

NMR Spectrum (CDCl$_3$, 60 MHz): δ1.22(t,J=7 Hz,CH$_2$CH$_3$), 2.94(q,J=7 Hz,CH$_2$CH$_3$), 4.76(s,CH), 5.32(s,CH$_2$O), 7.24–8.36(m,ar.H$_4$).

REFERENCE EXAMPLE 10

Di-t-butyl 2-diazoacetonedicarboxylate

A solution consisting of 2.6 g of di-t-butyl acetonedicarboxylate, 2 g of tosyl azide, 1.4 ml of triethylamine and 40 ml of ether is stirred for 16 hours at room temperature, which is mixed with 40 ml of ethyl acetate. The mixture is washed with 50 ml of water, then with a saturated aqueous solution of sodium chloride (50 ml×2), and dried over magnesium sulfate, followed by concentration under reduced pressure to the half volume. Then toluenesulfonamide precipitated is removed by filtration with suction, and the filtrate is concentrated to dryness under reduced pressure. The oily residue is subjected to silica-gel column chromatography (dichloromethane), and the fractions containing the desired product are collected, which is concentrated to dryness under reduced pressure to give 2.6 g (yield 96%) of the titled compound as an oily substance.

IR Spectrum $\nu_{max}$(neat): 2990, 2140, 1740(sh), 1720, 1660, 1480, 1460, 1400 cm$^{-1}$.

NMR Spectrum (CDCl$_3$, 60 MHz) δ: 1.46(s,C(CH$_3$)$_3$), 1.50(s,C(CH$_3$)$_3$), 3.73(s,CH$_2$CO$_2$).

REFERENCE EXAMPLE 11

Bis(p-nitrobenzyl) acetonedicarboxylate

A mixture of 1.0 g of citric anhydride and 5 ml of dichloroethane is stirred, to which is added dropwise 1.1 ml of chlorosulfonic acid. The mixture is stirred for one hour and left standing overnight. The mixture is then stirred under ice-cooling, to which is added a mixture consisting of 6 g of p-nitrobenzylalcohol and 30 ml of dichloroethane, followed by stirring at room temperature. The reaction mixture is poured into cracked ice and stirred. The organic layer is separated, washed with water twice, dried over anhydrous magnesium sulfate, and concentrated under reduced pressure. The oily residue is subjected to silica-gel column-chromatography twice (first: dichloromethane-ethyl acetate=19:1, second: dichloromethane-n-hexane-ethyl acetate=17:2:1). The fractions containing the desired product are combined, which is concentrated to dryness to give 1.04 g (yield 48%) of the titled compound as crystals, m.p. 85°–87° C.

IR Spectrum $\nu_{max}$(KBr): 1758, 1735, 1724, 1612, 1520 cm$^{-1}$.

NMR Spectrum (CDCl$_3$, 60 MHz) δ: 3.80(s,2×CH$_2$), 5.36(s,2×OCH$_2$-ar.), 7.98(ABq,J=9 & 42 Hz,ar.H$_8$).

REFERENCE EXAMPLE 12

Methyl [3R,4S]-2-(4-chloro-3-phthalimido-2-oxoazetidin-1-yl)-2-oxoacetate

A solution of 1.8 g of methyl [3R,4S]-2-(4-chloro-3-phthalimido-2-oxoazetidin-1-yl)-2-isopropylidenylacetate, prepared according to procedures described in "Can. J. Chem., 50, 2894 (1972) (W. Wolfe et al.,)," in 35 ml of dichloromethane is stirred at −78° C., and ozone is allowed to pass through the solution for 20 minutes, then nitrogen gas is allowed to pass through the solution for 1 hour. The reaction solution is shaken with 5 ml of an aqueous solution of 0.5 g of sodium bisulfite. The organic layer is separated, washed with a saturated aqueous solution of sodium chloride, dried over anhydrous magnesium sulfate and concentrated under reduced pressure to afford the titled compound.

IR Spectrum $\nu_{max}$(KBr): 3450, 2975, 1840, 1780, 1760, 1720, 1400, 1350, 1260, 1200, 1130, 1100, 970, 795, 770, 720 cm$^{-1}$.

NMR Spectrum (CDCl$_3$, 60 MHz) δ: 3.98(s,OCH$_3$), 5.70(d,J=2.4 Hz,3—H), 6.22(d,J=2.4 Hz,4—H), 7.88(s,aromatic).

$[\alpha]_D^{24.5°} = +41.8°$ (c=0.685, CHCl$_3$).

REFERENCE EXAMPLE 13

Methyl [3R,4R]-2-(3-benzyloxycarbonylamino-4-chloro-2-oxoazetidin-1-yl)-2-isopropylidenylacetate A solution of 55 g of methyl 6β-benzyloxycarbonylaminopenicillanate in 200 ml of dichloromethane is stirred at −78° C., to which is added dropwise 470 ml of 1 Mol chlorine-carbon tetrachloride solution over 20 min. After raising the temperature of the solution to 0° C. during 1 hr, the solution is concentrated under reduced pressure. The residue is subjected to silica-gel chromatography by use of n-hexane-ethyl acetate (2:1) as an eluent. The fractions containing the desired compound are collected and concentrated to afford the titled compound as an oil.

IR Spectrum $\nu_{max}$(neat): 3350, 1780, 1730, 1700 cm$^{-1}$.

NMR Spectrum (CDCl$_3$, 60 MHz) δ: 2.00 & 2.26(each s,C(CH$_3$)$_2$), 3.70(s,OCH$_3$), 4.85(q,J=2 & 9 Hz,3—H), 5.15(s,OCH$_2$), 5.80(d,J=2 Hz,4—H), 6.25(d,J=9 Hz,NH), 7.30(s,aromatic H$_5$).

TLC, Rf; 0.36/n-hexane: AcOET=2:1, Merck TLC plate 60 F$_{254}$, (Germany).

EXAMPLE 1

[3S,4S]-4-Bisacetylmethyl-3-(1-hydroxyisopropyl)-2-oxoazetidine

A solution of 1.5 g (4 mMol) of pivaloyloxymethyl [3R,4S]-2-[4-chloro-3-(1-hydroxyisopropyl)-2-oxoazetidin-1-yl]-2-isopropylidenylacetate in 50 ml of dichloromethane is stirred at −78° C., to which is introduced ozone for 15 minutes. Consumption of the starting material is cofirmed by means of thin-layer chromatography. Introduction of nitrogen gas into the reaction mixture for 30 minutes gives a solution containing pivaloyloxymethyl [3R,4S]-2-[4-chloro-3-(1-hydroxyisopropyl)-2-oxoazetidin-1-yl]-2-oxoacetate. This solution is stirred at −10° C., to which are added 800 mg (8 mMol) of acetylacetone, then 20 ml of methanol dissolving 216 mg (4 mMol) of sodium methylate. The solvent is distilled off under reduced pressure, and the residue is stirred vigorously together with 20 ml of ethyl acetate, 1 ml of 1 N-hydrochloric acid and 10 ml of a saturated aqueous solution of sodium chloride. The organic layer is separated, dried over magnesium sulfate, and concentrated. The resulting reaction product is subjected to silica-gel column-chromatography (n-hexane-ethyl acetate 1:1–1:4). The fractions containing the desired product are combined and concentrated to give 80 mg of the titled compound as crystals, m.p. 109°–110° C.

Elemental analysis: C$_{11}$H$_{17}$NO$_4$

|  | C (%) | H (%) | N (%) |
| --- | --- | --- | --- |
| Calcd. | 55.91 | 7.68 | 5.93 |
| Found | 55.86 | 7.37 | 6.02 |

IR Spectrum $\nu_{max}$(KBr): 3350, 3175, 3120, 1740, 1700, 1360, 1180, 965, 840 cm$^{-1}$.

NMR Spectrum (CDCl$_3$, 90 MHz) δ: 1.27 and 1.30(each s,C(CH$_3$)$_2$), 1.7(br.s,OH), 2.23 and 2.30(each s,2×COCH$_3$), 2.90(d,J=1.8 Hz,3—H), 3.82(d,J=9 Hz,CH), 4.41(q,J=1.8 and 9 Hz,4—H), 6.20(br.NH).

EXAMPLE 2-4

In place of acetylacetone in Example 1, 8 mMol each of carbon acids having the formula,

wherein R$^2$, R$^3$ and R$^4$ are respectively as defined in the following table, is employed, and the procedure of Example 1 is repeated to give the corresponding 4-substituted-2-oxoazetidines as shown in the following table involving their physico-chemical constants as well.

| Ex. No. | R² | R³ | R⁴ | IR Spectrum $\nu_{max}$ cm$^{-1}$ | NMR Spectrum δ | $a_D$ (c, solvent) |
|---|---|---|---|---|---|---|
| 2 | H | CH₃CO— | CH₃OCO— | (KBr): 3450, 3350, 2980, 1750, 1730, 1440, 1385, 1370, 1310 | (CDCl₃,60MHz): 1.28(m,C(CH₃)₂), 2.27 & 2.33(each s,CH₃CO), 2.62(br.s,OH), 3.00(d,J=1.6 Hz,3-H), 3.62(d, J=8Hz,CH), 3.77(s, CH₃O), 4.11(dd,J= 1.6 & 8Hz,4-H), 6.47(br.s,NH) | — |
| 3 | H | —CN | —CN | (KBr): 3350, 2990, 2200 1760, 1690, 1650, 1380, 1170 | (CD₃OD,90MHz): 1.27 & 1.35(each s,C(CH₃)₂), 2.87 (s,OH), 3.23(d,J= 1.8Hz,3-H), 4.07 (d,J=7.2Hz,CH), 4.21(dd,J=1.8 & 7.2Hz,4-H), 6.68 (d,J=1.8Hz,NH) | — |
| 4 | C₆H₅S— | C₂H₅SCO— | O₂N—C₆H₄—CH₂OCO— | (KBr):3420 1762, 1740, 1662, 1525 | (CDCl₃, 60MHz): 1.26 & 1.29(each t,J=7Hz,CH₂CH₃), 1.36(s,C(CH₃)₂), 2.33 & 2.65(each br.s,OH), 2.92 & 2.95(each q,J= 7Hz,CH₂CH₃), 3.32 & 3.59(each d,J= 2Hz,4-H), 4.32(d, J=2Hz,3-H), 4.75 & 4.95(each ABq, 2H,J=13.33 & 13.23 Hz,OCH₂), 6.30 & 6.50(each br.s, NH), 7.10–8.20 (m,ar.H₄) | +8.9° (0.66, chloroform) |

EXAMPLE 5

[3R,4R]-4-(1-Acetyl-1-methoxycarbonyl)methyl-3-phthalimido-2-oxoazetidine

A mixture of 348 mg (3 mMol) of methyl acetoacetate and 5 ml of 0.2 Mol methanolic sodium methylate is stirred at −78° C., to which is added dropwise a solution of 336 mg (1 mMol) of methyl [3R,4R]-2-(4-chloro-3-phthalimido-2-oxoazetidin-1-yl)-2-oxoacetate in 2 ml of tetrahydrofuran. To the mixture is added 60 mg of acetic acid, followed by concentration under reduced pressure. The residue is shaken together with 20 ml of ethyl acetate and 10 ml of a saturated aqueous solution of sodium chloride. The organic layer is separated, and dried over magnesium sulfate, followed by concentration. The resulting reaction product is subjected to silica-gel column-chromatography (n-hexane-ethyl acetate=1:1–1:4 V/V). The fractions containing desired product are combined and concentrated to give 227 mg of the titled compound as crystals, m.p. 160°–160.5° C. (decomp.)

Elemental analysis: C₁₆H₁₄N₂O₆·0.25H₂O

|  | C (%) | H (%) | N (%) |
|---|---|---|---|
| Calcd. | 57.40 | 4.37 | 8.37 |
| Found | 57.23 | 4.26 | 8.23 |

IR Spectrum $\nu_{max}$(KBr): 3300, 1790, 1770, 1740, 1710, 1400, 730 cm$^{-1}$.

NMR Spectrum (d₆-DMSO, 90 MHz) δ: 2.23 & 2.27(each s,CH₃CO), 3.27(br.s,OH), 3.58 & 3.70(each s,OCH₃), 4.32(s,4—H), 5.23(s,3—H), 7.90(s,ar.H₄), 8.67(s,NH).

Thin layer chromatography on silica gel plate 60 F₂₅₄ (Merck, Germany) Rf=0.12 (n-hexane: AcOEt=1:1)

EXAMPLE 6–14

In place of methyl acetoacetate in Example 5, 3 mMol each of carbon acids having the formula,

wherein R², R³ and R⁴ are respectively as defined in the following table is employed, and the procedure of Example 5 is repeated to give the corresponding [3R,4R]-

4-substituted-3-phthalimido-2-oxoazetidines as shown in the following table involving physico-chemical constants as well.

| Ex. No. | $R^2$ | $R^3$ | $R^4$ | IR Spectrum $\nu_{max}$cm$^{-1}$ | NMR Spectrum $\delta$ | $\alpha_D$ (c. solvent) |
|---|---|---|---|---|---|---|
| 6 | H | $CH_3CO-$ | $CH_3CO-$ | (KBr): 3275, 1780, 1770, 1750, 1710, 1400, 1360, 1280, 720 | (d$_7$-DMF,90MHz): 2.30 & 2.32(each s,CH$_3$), 4.45(dd,J=2.4 & 9Hz, 4-H), 4.62(d,J=9Hz, CH), 5.22(d,J=2.4 Hz,3-H), 7.92(ar. H$_4$), 8.57(s,NH) | +12.3° (0.43, dioxane) |
| 7 | H | $ClCH_2CO-$ | $C_2H_5OCO-$ | (KBr): 3290, 2990, 2950, 1785, 1760, 1740, 1710, 1390, 1190, 725 | (d$_6$-DMSO,90MHz): 1.08 & 1.22(each t,J=6Hz, CH$_3$), 3.9–4.6(m, —CH$_2$Me, & CH), 4.40(s, 4-H), 4.63(s,ClCH$_2$CO), 5.25(d,J=2.4Hz,3-H), 7.92(s,ar.H$_4$), 8.63 & 8.72(each s,NH) | −45.8° (0.38, dioxane) |
| 8 | H | $CH_3CO-$ | $(CH_3)_3COCO-$ | (CHCl$_3$):1785, 1730, 1400, 1375, 1300, 1145 | (CDCl$_3$,90MHz): 1.42 & 1.50(each s,C(CH$_3$)$_3$), 2.33(s,CH$_3$CO), 3.72 (q,J=2.4 & 9Hz,COCH—CO), 4.51(q,J=2.4 & 9Hz,COCHCO), 4.56(q, J=2.4 & 9Hz,4-H), 5.05 & 5.18(each d,J=2.4Hz 3-H), 6.45(br.s,NH), 7.65–7.95(m,ar.H$_4$) | |
| 9 | H | $CH_3OCO-$ | $CH_3OC(=O)-C(=N_2)-C(=O)-$ | (KBr): 3350, 2970, 2150, 1795, 1765, 1725, 1710, 1660, 1390, 1340, 1200 | (CD$_3$CN,90MHz): 3.57, 3.67, 3.78 & 3.80 (each s, 2×CH$_3$), 4.33–4.53(m-4H), 4.75(d, J=9Hz,½CH of diastereoisomer), 4.78 (d,J=7.5Hz,½CH of diastereoisomer), 5.25 & 5.32(each d, J=2.4Hz,3-H), 6.82 & 6.93(each br.s,NH), 7.83(s,ar.H$_4$) | +14.2° (0.26, dioxane) |
| 10 | H | $C_2H_5SCO-$ | $O_2N-C_6H_4-CH_2OCO-$ | (KBr): 3400, 1786, 1768, 1730, 1720, 1670 | (CDCl$_3$+d$_6$-DMSO, 60MHz): 1.24(t,J=7Hz,CH$_2$), 2.96(q, J=7Hz,CH$_2$), 4.11(d, J=9Hz,CH), 4.58(dd, J=2 & 9Hz,4-H), 5.20(br,s,3-H & —CH$_2$—(PNB), 7.24–8.10(m,ar.H$_8$), 8.30 (s,NH) | +35.5° (1.04, dioxane) |
| 11 | $C_6H_5S-$ | t-$C_4H_9OCO-$ | t-$C_4H_9OCOCH_2CO-$ | (KBr): 3400, 1788, 1726, 1395 | (CDCl$_3$,60MHz): 1.47 & 1.54(each s, 2×C(CH$_3$)$_3$), 3.80 & 3.94(ABq & t,J= 16.32 & 16Hz, total 2H,CH$_2$), 4.38 & 4.55(each d, J=2.5Hz,total 1H, 4-H), 5.67 & 5.76 (each d,J=2.5Hz, total 1H,3-H), 6.25 & 6.53(each br.s.1H,NH), 7.02–7.81(m,9H,ar.) | |
| 12 | H— | $ClCH_2CO-$ | t-$C_4H_9OCO-$ | (KBr): 3350, 2990, 2950, 1780, 1770, 1760, 1740, 1730, 1715, 1390, 1370 | (CDCl$_3$,60MHz): 1.42(s,C(CH$_3$)$_3$), 4.17(d,J=9Hz, COCHCO), 4.40(s, ClCH$_2$CO), 4.70(dd, J=2.8 & 9Hz,4-H), 5.33(d,J=2.3Hz, 3-H), 6.70(br.s. | |

-continued

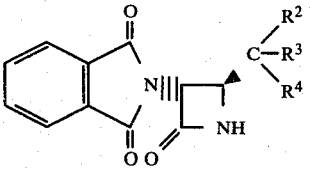

| Ex. No. | R² | R³ | R⁴ | IR Spectrum $\nu_{max}$cm⁻¹ | NMR Spectrum δ | $\alpha_D$ (c. solvent) |
|---|---|---|---|---|---|---|
| 13 | H— | C₆H₅SCH₂CO— | C₂H₅OCO— | (KBr): 3350, 2990, 1785, 1720, 1390, 720 | NH), 7.90 & 7.93 (2×s,ar.H₄) (CDCl₃,60MHz): 1.17 & 1.23(2×t, J=7.5Hz,CH₂CH₃), 4.02(s,SCH₂), 3.9–4.3(m,4-H & CH₂CH₃), 4.50 & 4.53(2×d,J=10Hz, COCHCO), 5.23 & 5.33(2×d,J=2.8Hz, 3-H), 6.57 & 7.00(2×br.s,NH), 7.42(s,C₆H₅), 7.90 & 7.93(2×s, phthalimido H₄) | +5.9° (0.56, dioxane) |
| 14 | C₆H₅S— | CH₃OCO— | Cl₃CCH₂OCO— | (KBr): 3300, 2960, 1800, 1770, 1720, 1400, 1260, 1160, 790 760, 725 | (CDCl₃,90MHz): 3.67 & 3.78(2s, CH₃), 4.55 & 4.85 (ABq,J=12Hz, CH₂CCl₃), 4.72 & 4.75(2d,J=2.4Hz, 4-H), 5.82 & 5.85 (2d,J=2.4Hz,3-H), 6.33(br.s,NH), 7.2–8.0(m,ar.H₄) | +40.9° (1.225, chloroform) |

EXAMPLE 15

[3R,4R]-3-Bromo-4-(1-acetyl-1-t-butyloxycarbonyl)-methyl-2-oxoazetidine

A solution of 890 mg (3 mMol) of methyl [3S,4R]-2-(3-bromo-4-chloro-2-oxoazetidin-1-yl)-2-isopropylidenylacetate in 60 ml of dichloromethane is stirred at −78° C. Ozone is allowed to pass through the solution for one hour. Consumption of the starting material is confirmed by means of thin-layer chromatography. Then, nitrogen gas is allowed to pass through the reaction mixture for 30 minutes to give a solution of methyl [3S,4R]-2-(3-bromo-4-chloro-2-oxoazetidin-1-yl)-2-oxoacetate. This solution is cooled to −78° C., to which is added dropwise a mixture of 0.497 ml of t-butyl acetoacetate and 15 ml of 0.2 N-methanolic sodium methylate, followed by stirring for 20 minutes. To the mixture is added 0.5 ml of acetic acid, then the reaction mixture is concentrated under reduced pressure. The oily residue is shaken together with 200 ml of ethyl acetate and 50 ml of water. The organic layer is separated, washed with a saturated aqueous solution of sodium chloride (3×20 ml), dried over magnesium sulfate, and concentrated under reduced pressure. The resulting product is subjected to silica-gel column-chromatography (n-hexane:ethyl acetate=1:1). The fractions containing the desired compound are combined, and concentrated to give 670 mg of the titled compound as an oily substance.

Elemental analysis: C₁₁H₁₆BrNO₄·H₂O

|  | C (%) | H (%) | N (%) |
|---|---|---|---|
| Calcd. | 40.77 | 5.60 | 4.32 |
| Found | 40.93 | 5.06 | 3.81 |

IR Spectrum $\nu_{max}$(neat): 3300, 2995, 1780, 1720, 1460, 1375, 1260, 1150, 1100, 1040, 840 cm⁻¹.

NMR Spectrum (CDCl₃, 90 MHz) δ: 1.50 & 1.53(each s,C(CH₃)₃), 2.30, 2.33(each s,COCH₃), 3.61(d,J=10 Hz,½×CH of diastereoisomer), 3.78(d,J=8 Hz,½×CH of diastereoisomer), 4.16(dd,J=1.5 & 10 Hz,½4—H), 4.19(dd,J=1.5 & 8 Hz,½4—H), 4.64 & 4.68(each d,J=1.5 Hz,3—H), 6.97(br.s,NH).

EXAMPLE 16

[3R,4R]-4-[1,3-Bis(t-butyloxycarbonyl)-3-diazo-2-oxopropyl]-3-bromo-2-oxoazetidine A solution of 1.49 g (5 mMol) of methyl [3S,4R]-2-(3-bromo-4-chloro-2-oxoazetidin-1-yl)-2-isopropylidenylacetate in 100 ml of dichloromethane is stirred at −78° C. Ozone is allowed to pass through the solution for 30 minutes until the complete consumption of the starting material is observed by thin-layer chromatography. Then, nitrogen gas is allowed to pass through the reaction mixture for about 30 minutes to give a solution containing methyl [3S,4R]-2-(3-bromo-4-chloro-2-oxoazetidin-1-yl)-2-oxoacetate. This solution is cooled at −78° C., to which is added dropwise a solution of 1.36 g (5 mMol) of di-t-butyl α-diazoacetone-dicarboxylate and 25 ml (5 mMol) of 0.2 N-sodium methylate in 10 ml of dichloromethane, followed by stirring for 20 minutes. To the reaction mixture is added 2 ml of acetic acid, which is then concentrated under reduced pressure. The residue is shaken together with 150 ml of ethyl acetate and 50 ml of water. The organic layer is washed with a saturated aqueous solution of sodium chloride (3×50 ml), dried over anhydrous magnesium sulfate, and concentrated under reduced pressure. The resulting product is subjected to silica-gel chromatography (n-hexane:ethyl acetate 2:1-1:1). The fractions containing the desired product are combined, and concentrated to give 1.11 g of the titled compound as an oily substance. The product is left standing at a refrigerator to cause partial crystallization. Analytical data on the resulting crystals are as follows: m.p. 136°–138° C.

Elemental analysis: $C_{16}H_{22}BrN_3O_6$

|  | C (%) | H (%) | N (%) |
|---|---|---|---|
| Calcd. | 44.46 | 5.13 | 9.72 |
| Found | 44.40 | 5.08 | 9.82 |

IR Spectrum $\nu_{max}$(KBr): 3400, 3220, 2990, 2150($N_2$), 1765, 1740, 1720, 1665, 1375, 1340, 1260, 1210, 1160, 1140, 1090 cm$^{-1}$.

NMR Spectrum (CDCl$_3$, 90 MHz) δ: 1.45(s,C(CH$_3$)$_3$), 1.51(s,C(CH$_3$)$_3$), 4.19(dd,J=2 & 5 Hz,4—H), 4.63(d,J=5 Hz,CH), 4.90 & 4.88(each d,J=2 Hz,3—H), 6.28(br.s,NH).

$[\alpha]_D^{23°} +114.4°$ (c=0.825, CHCl$_3$).

EXAMPLE 17

[3R,4R]-4-[1-t-Butoxycarbonyl-2-oxo-3-diazo-3-(2,2,2-trichloroethoxycarbonyl)propyl]-3-phthalimido-2-oxoazetidine A mixture consisting of 1.52 g of 2,2,2-trichloroethyl 2-(2-t-butoxycarbonylacetyl)-2-diazoacetate, 2 ml of dichloromethane and 20 ml of 0.2 M methanolic sodium methylate is stirred at −70° C. To the mixture is added at one portion 1.6 g of methyl [3S,4R]-2-[4-(4-chloro-3-phthalimido-2-oxoazetidin-1-yl)]-2-oxoacetate, followed by immediate addition to the reaction mixture 10 drops of acetic acid. The resulting mixture is concentrated under reduced pressure. The oily residue is vigorously shaken together with 5 ml of ethyl acetate and 5 ml of a saturated aqueous solution of sodium chloride. The organic layer is subjected to silica-gel column chromatography (n-hexane-ethyl acetate=1:1). The fractions containing the desired compound are combined, and concentrated to give 2.4 g (yield: 85.4%) of the titled compound as a powder.

Elemental analysis: $C_{22}H_{19}Cl_3N_4O_8 \cdot H_2O$

|  | C (%) | H (%) | N (%) |
|---|---|---|---|
| Calcd. | 44.65 | 3.58 | 9.47 |
| Found | 44.42 | 3.64 | 8.91 |

IR Spectrum $\nu_{max}$(KBr): 3350, 2150, 1790, 1770, 1720, 1660, 1390, 1340, 1300, 1160, 720 cm$^{-1}$.

NMR Spectrum (CDCl$_3$, 90 MHz) δ: 1.34 & 1.47(each s,C(CH$_3$)$_3$), 4.5–4.8 & 4.8–5.1(each m,4—H,CH$_2$CCl$_3$ & COCHCO), 5.25 & 5.32(each d,J=2.4 Hz,3—H), 6.35 & 6.47(each br.s,NH), 7.8–8.0(-m,ar.H$_4$).

$[\alpha]_D^{23°} +19.5°$ (c=0.425, CHCl$_3$).

EXAMPLE 18

[3R,4R]-4-(1-Ethylthiocarbonyl-1-p-nitrobenzyloxycarbonyl-1-phenylthio)methyl-3-phthalimido-2-oxoazetidine A solution of 363 mg of methyl [3S,4R]-2-(4-chloro-3-phthalimido-2-oxoazetidin-1-yl)-2-isopropylidenylacetate in 50 ml of dichloromethane is stirred at −70° C. Ozone is allowed to pass through the solution (for about 15 minutes) until complete consumption of the starting material is observed by means of thin-layer chromatography. Nitrogen gas is allowed to pass through the reaction mixture for about 30 minutes to give a solution containing methyl [3S, 4R]-2-(4-chloro-3-phthalimido-2-oxoazetidin-1-yl)-2-oxoacetate. This solution is stirred at −70° C., to which are added dropwise 2 ml of methanol and a mixture consisting of 210 mg of p-nitrobenzyl 2-ethylthiocarbonyl-2-phenylthioacetate, 2 ml of dichloromethane and 3 ml of 0.2 M methanolic sodium methylate. To the reaction mixture are added, after stirring for 20 minutes, 0.5 ml of 2 N-HCl and 3 ml of methanol. The mixture is washed with ice-water, then with a saturated aqueous solution of sodium chloride, followed by concentration under reduced pressure. The oily residue is subjected to silica-gel column chromatography (n-hexane-ethyl acetate=1:1). The fractions containing the desired product are combined and concentrated to afford 69 mg of the titled compound as a powder.

IR Spectrum $\nu_{max}$(KBr): 3415, 1798, 1721, 1524 cm$^{-1}$.

NMR Spectrum (CDCl$_3$, 60 MHz) δ: 1.27(t,J=7 Hz, CH$_2$CH$_3$), 2.97 & 3.00(each q,J=7 Hz,CH$_2$CH$_3$), 4.74 & 4.85(each d,J=2.5 Hz,4—H), 4.98(ABq,J=13 & 18 Hz,—OCH$_2$), 5.80 & 6.00(each d,J=2.5 Hz, 3—H), 6.63 & 6.70(each br.s,NH), 7.16–8.24(m,13H,ar.).

EXAMPLE 19

[3R,4R]-4-[1,3-Bis(t-butyloxycarbonyl)-3-diazo-2-oxopropyl]-3-phthalimido-2-oxoazetidine A solution of 725 mg of methyl [3S,4R]-2-(4-chloro-3-phthalimido-2-oxoazetidin-1-yl)-2-isopropylidenylacetate in 100 ml of dichloromethane is stirred at −78° C. Ozone is allowed to pass through the solution (for about 30 minutes) until complete consumption of the starting material is observed by means of thin-layer chromatography. Nitrogen gas is then allowed to pass through the reaction mixture for 30 minutes to give a solution containing methyl [3S,4R]-2-(4-chloro-3-phthalimido-2-oxoazetidin-1-yl)-2-oxoacetate. This solution is stirred at −78° C., to which is added dropwise a solution consisting of 545 mg of di-t-butyl 2-diazoacetonedicarboxylate, 10 ml of 0.2 N methanolic sodium methylate and 10 ml of methanol. To the reaction mixture, after stirring for 20 minutes, is added 1 ml of acetic acid, followed by concentration under reduced pressure. The oily residue is dissolved in 100 ml of ethyl acetate, and the solution is washed with 50 ml of water, then with a saturated aqueous solution of sodium chloride (20 ml×3), followed by concentration under reduced pressure. The oily residue is subjected to silica-gel column chromatography (n-hexane-ethyl acetate=1:1). The fractions containing the desired compound are combined and concentrated to dryness to afford 400 mg (yield 41%) of the titled compound as an oily substance.

Elemental analysis: $C_{24}H_{26}N_4O_7 \cdot 2H_2O$

|  | C (%) | H (%) | N (%) |
|---|---|---|---|
| Calcd. | 55.59 | 5.83 | 10.81 |
| Found | 55.75 | 5.36 | 10.02 |

IR Spectrum $\nu_{max}$(KBr): 3400, 2990, 2140, 1790, 1770, 1720, 1645, 1400, 1370 cm$^{-1}$.

NMR Spectrum (CDCl$_3$, 100 MHz) δ: 1.48 & 1.56(each s,2x C(CH$_3$)$_3$), 4.48 & 4.56(each d,J=2 Hz, 4—H), 4.68 (s,enol OH), 5.28 & 5.34(each d,J=2 Hz,3—H), 6.16 & 6.36(each br.s,NH), 7.6-8.0(m,ar.H4).

EXAMPLE 20

[3S,4S]-4-(1-Acetyl-1-methoxycarbonyl)methyl-3-phthalimido-2-oxoazetidine

To the solution of 10 ml of 0.2 M methanolic sodium methoxide cooled at −78° C., are added dropwise with stirring 696 mg (6 mMol) of methyl acetoacetate and 672 mg (2 mMol) of methyl [3R,4S]-2-(4-chloro-3-phthalimido-2-oxoazetidin-1-yl)-2-oxoacetate in 4.6 ml of dichloromethane. After 3 min, 10 drops of acetic acid are added. The solution is evaporated under reduced pressure and the residue is taken into ethyl acetate, washed with water and dried over anhydrous magnesium sulfate. The solution is evaporated to dryness, the resulting residual solids are triturated with ethyl ether and collected with suction to afford 441 mg (Y=54%) of the titled compound, m.p. 158°-159° C. (dec.).

IR Spectrum $\nu_{max}$(KBr): 3325, 1795, 1765, 1740, 1710, 1400, 1300, 730 cm$^{-1}$.

NMR Spectrum (CDCl$_3$, 90 MHz) δ: 2.23 & 2.27(each s,COCH$_3$ doublet is due to enolization), 3.58 & 3.70(each s,OCH$_3$), 4.33(s, 4—H & OH), 5.23(s,3—H), 7.95(s,aromatic), 8.72(s,NH).

EXAMPLE 21-26

In place of methyl acetoacetate in Example 20, 6 mMol of each of carbon acids represented by the formula

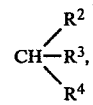

wherein R$^2$, R$^3$ and R$^4$ are respectively defined in the following table, is employed and the procedure of Example 5 is repeated to give the corresponding [3S,4S]-3-phthalimido-4-substituted-2-oxoazetidines as shown in the following table involving their physico-chemical constants as well.

| Ex. No | R$^2$ | R$^3$ | R$^4$ | IR Spectrum $\nu_{max}$cm$^{-1}$ | NMR Spectrum δ | $\alpha_D$ (c, solvent) |
|---|---|---|---|---|---|---|
| 21 | H | t-C$_4$H$_9$OCO— | ClCH$_2$CO— | (KBr): 3330, 2990,2950, 1780,1740, 1720,1390, 1160, 725 | (CDCl$_3$,90MHz): 1.43(s,(CH$_3$)$_3$C), 4.10(d,J=9.6Hz, —COCHCO—), 4.30 (s,ClCH$_2$), 4.63 (dd,J=3 & 9.6Hz, 4-H), 5.25(d, J=3Hz,3-H), 6.58 (br.s,NH), 7.85 (m,aromatic) | +70.9° (0.485, CHCl$_3$) |
| 22 | H | ClCH$_2$CO— | C$_2$H$_5$OCO— | (KBr): 3275, 2990, 2950, 1785, 1770, 1760, 1740, 1715, 1390, 1185, 720 | (d$_6$-DMSO,90MHz): 1.07 & 1.22(each t,CH$_3$CH$_2$), 4.07 & 4.18(each t, J=7.2Hz,CH$_3$CH$_2$), 4.35-4.65(m,4H & —COCHCO—), 4.67(s,ClCH$_2$), 5.30(m,3-H), 7.95(s,aromatic), 8.72 & 8.78(each s,NH) | +36.7° (1.115, dioxane) |
| 23 | H | CH$_3$CO— | t-C$_4$H$_9$OCO— | (KBr): 3250, 2980, 1775, 1720, 1470, 1400, 1375, 1140, 720 | (CDCl$_3$,90MHz): 1.42 & 1.48(each s,(CH$_3$)$_3$C),2.33 (s,CH$_3$CO), 3.73 & 3.78(each d, J=9.6Hz,—COCHCO— 4.52 & 4.57 (each dd, J=3 & 9.6Hz, 4-H), 5.08 & 5.20(each d,J= 3Hz,3-H), 6.6 (br.s,NH),7.82 (m,aromatic) | +14.3° (0.91, CHCl$_3$) |
| 24 | C$_6$H$_5$S— | O$_2$N—⟨⟩—CH$_2$OCO— | O$_2$N—⟨⟩—CH$_2$OCO— | (KBr): 3270, 1790, 1735, 1720, 1525, 1400, 1350 | (CDCl$_3$,90MHz): 4.72(d,J=2.4Hz, 4-H),4.93 & 5.10 (ABq,J=12.6Hz, | |

| Ex. No | R² | R³ | R⁴ | IR Spectrum $\nu_{max}$cm⁻¹ | NMR Spectrum δ | $\alpha_D$ (c, solvent) |
|---|---|---|---|---|---|---|
| | | | | 1260 | CH₂—C₆H₄—NO₂), 5.33(s,CH₂—C₆H₄—NO₂), 6.67(s, NH), 6.9–8.25 (m,aromatic) | |
| 25 | H | t-C₄H₉OCO— | Cl₃CCH₂OCO— | (KBr): 3350, 2980, 2150, 1780, 1720, 1655, 1380, 1335, 1300, 1150, 720 | (CDCl₃,90MHz): 1.37 & 1.47(each s, (CH₃)₃C), 4.5–4.8 (m,—COCHCO—),4.90 & 4.95(each s, CH₂CCl₃), 5.30 & 5.35 (each d,J=2.4Hz, 3-H), 6.50 & 6.60 (each br.s,NH),7.8–8.0(m,aromatic) | −19.5° (1.02, CHCl₃) |
| 26 | H | CH₃CO— | CH₃CO— | (Nujol): 3250, 1780, 1730, 1710, 1400, 1380, 660 | (CDCl₃, 60MHz): 2.06 & 2.30(each s, CH₃), 3.23–3.40(m, —COCHCO—), 4.40(d, J=2Hz,4-H), 5.15(d, J=2Hz,3-H), 7.75(s, aromatic H₄) 8.60 (s,NH) | −42.5° (0.975, DMSO) |

EXAMPLE 27

[3S,4S]-4-[1-t-Butoxycarbonyl-3-diazo-2-oxo-3-(2,2,2-trichloroethoxycarbonyl)propyl]-3-(1-hydroxyisopropyl)-2-oxoazetidine To 50 ml of 0.2 M methanolic sodium methoxide solution stirred and cooled at −78° C., are successively added 3.43 g of 2,2,2-trichloroethyl 4-t-butyloxycarbonyl-2-diazo-3-oxobutyrate in 30 ml of dichloromethane and 10 mMol equivalent of pivaloyloxymethyl [3R,4S]-2-[4-chloro-3-(1-hydroxyisopropyl)-2-oxoazetidin-1-yl]-2-oxoacetate, which is prepared according to the procedure of Example 1, in 30 ml of dichloromethane. After a few minutes, 0.6 ml of acetic acid is added to the solution and the solution is evaporated to dryness under reduced pressure. The residue is taken into 50 ml of ethyl acetate, washed with water, and dried over anhydrous magnesium sulfate, followed by concentration under reduced pressure to give the crude product. The product is subjected to silica-gel column chromatography by use of n-hexane-ethyl acetate=1:2 for elution. The fractions containing the desired compound are combined and concentrated to give 2.6 g of the titled compound.

IR Spectrum $\nu_{max}$(neat): 3350(br.), 2980, 2150, 1740(br.), 1660, 1375, 1150, 1050 cm⁻¹.

$[\alpha]_D^{22.5°} = -13.0°$ (c=0.795, CHCl₃).

EXAMPLE 28

[3R,4R]-4-(1-Benzhydryloxycarbonyl-3-diazo-4-methoxycarbonyl-2-oxopropyl)-3-phthalimido-2-oxoazetidine To 10 ml of 0.2 M methanolic sodium methoxide solution stirred and cooled at −70° C., are successively added 704 mg of methyl 4-benzhydryloxycarbonyl-2-diazo-3-oxobutyrate in 1 ml of dichloromethane and 672 mg of methyl [3S,4R]-2-(4-chloro-3-phthalimido-2-oxoazetidin-1-yl)-2-oxoacetate in 1 ml of dichloromethane. After a few minutes, 3 drops of acetic acid is added to the solution and the solution is evaporated to dryness under reduced pressure. The residue is taken into 10 ml of ethyl acetate, washed with water and dried over anhydrous magnesium sulfate. The solution is concentrated under reduced pressure and the concentrate is subjected to silica-gel column-chromatography (n-hexane-ethyl acetate=1:1). The fractions containing the desired compound are combined and concentrated under reduced pressure to give 400 mg of the titled compound.

IR Spectrum $\nu_{max}$(KBr): 3350, 2960, 2150, 1790, 1770, 1720, 1650, 1390, 1210, 720, 700 cm⁻¹.

NMR Spectrum (CDCl₃, 90 MHz) δ: 3.90(s,CH₃), 4.4–5.4(m,3—H,4—H and —COCHCO—), 6.33 & 6.47(each, br.s,NH), 6.8–7.2(m,CH(Ph)₂), 7.37(s,aromatic), 7.7–8.0(m,aromatic).

$[\alpha]_D^{22°} = +20.0°$ (c=0.3, CHCl₃).

EXAMPLE 29–30

In place of methyl 4-benzhydryloxycarbonyl-2-diazo-3-oxobutyrate in Example 28, 2 mMol each of carbon acids having formula,

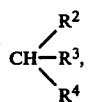

wherein R², R³ and R⁴ are respectively defined in the following table, is employed and the procedure of Example 28 are repeated to give the corresponding

[3R,4R]-4-substituted-3-phthalimido-2-oxo-azetidines as shown in the following table involving their physicochemical constants as well.

| Ex. No. | R² | R³ | R⁴ | IR Spectrum $\nu_{max}$cm⁻¹ | NMR Spectrum δ | $\alpha_D$ (c,solvent) |
|---|---|---|---|---|---|---|
| 29 | H | t-C₄H₉OCO— | CH₃OC(=O)—C(=N₂)—C(=O)— | (KBr): 3350, 2975, 2150, 1790, 1720, 1650, 1400, 1140, 800, 720 | (CDCl₃,60MHz): 1.4–1.7(m,(CH₃)₃C), 3.73, 3.83 & 3.97 (each s,CH₃), 4.72 (q,J=2 & 9Hz,4-H), 4.87(d,J=9Hz, —COCHCO—), 5.3–5.5 (m,3-H), 6.77 & 6.90(each br.s,NH) 7.90(s,aromatic) | +19.1° (0.45, CHCl₃) |
| 30 | H | t-C₄H₉OCO— | CH₃O—C₆H₄—CH₂OCC(=N₂)C(=O)— | (KBr): 3350, 2970, 2150, 1790, 1720, 1650, 1520, 1385, 1340, 1300, 1250, 1215, 1255, 1220, 1155, 725 | (CDCl₃,60MHz): 1.3–1.6(m,(CH₃)₃C), 3.90(s,OCH₃), 4.60 (q,J=2.4 & 8Hz, 4-H), 4.87(d,J=8Hz, —COCHCO—), 5.33(s, —CH₂—C₆H₄—), 5.45 (d,J=2.4Hz,3-H), 6.45 & 6.62(each br.s,NH), 7.00 & 7.45(each d,J=9Hz, aromatic), 7.88(s, aromatic) | +26.6° (0.935, CHCl₃) |

EXAMPLE 31

[3R,4R]-4-[(1-Acetyl-1-ethoxycarbonyl)ethyl]-3-phthalimido-2-oxoazetidine

To 10 ml of 0.2 M methanolic sodium methoxide cooled at −78° C., are added dropwise a solution of 864 mg of ethyl 2-methylacetoacetate and 672 mg (2 mMol) of methyl [3S,4R]-2-(4-chloro-3-phthalimido-2-oxoazetidin-1-yl)-2-oxoacetate in 5 ml of dichloromethane. After 3 min, 10 drops of acetic acid are added to the reaction mixture. The solvent is evaporated and the residue is taken into ethyl acetate, washed with water and dried over anhydrous magnesium sulfate. The solution is evaporated to dryness, the residue is subjected to silica-gel column chromatography (silica gel, 30 g) and developed with n-hexane-ethyl acetate (1:2). The fractions containing the desired compound are combined and concentrated, and the residue is triturated with ether to afford 200 mg of the titled compound. m.p. 135°–145° C.

IR $\nu_{max}$(neat): 3330, 2980, 1780, 1720, 1395, 1260, 1110, 915. 720 cm⁻¹.

NMR Spectrum (CDCl₃, 90 MHz) δ: 1.18 & 1.28(each t,J=14.4 Hz, CH₂CH₃), 1.52 & 1.53(each s,CH₃), 2.20 (s,COCH₃), 4.18 & 4.27(each q,J=14.4 Hz,CH₂CH₃), 4.53 & 4.57(d,J=3 Hz,4—H), 5.25 & 5.30(d,J=3 Hz,3—H), 6.25 & 6.62(each br.s,NH), 7.7–8.0(m,aromatic H₄).

EXAMPLE 32

[3R,4R]-3-Benzyloxycarbonylamino-4-(1,1-bisacetyl)-methyl-2-oxoacetidine

A solution of 28 g of methyl [3R,4R]-2-(3-benzyloxycarbonylamino-4-chloro-2-oxoazetidin-1-yl)-2-isopropylidenylacetate in 200 ml of dichloromethane is stirred at −70° C. Ozone is passed through the solution until the complete consumption of the starting material is observed by means of thin-layer chromatography, for which about 2 hr is required. Nitrogen gas is passed through the reaction solution for about 30 min to give a solution containing methyl [3R,4R]-2-(3-benzyloxycarbonylamino-4-chloro-2-oxoazetidin-1-yl)-2-oxoacetate.

This solution is stirred at −70° C., to which is added dropwise a solution consisting of 35 g of acetylacetone, 4.23 g of sodium methylate and 215 ml of methanol. After 3 min, 30 ml of acetic acid is added to the solution. The solvent is evaporated under reduced pressure and the residue is shaken with 200 ml of ethyl acetate and 200 ml of a saturated aqueous sodium chloride solution. The separated organic layer is dried over anhydrous sodium sulfate, followed by concentration. The residual solids are recrystallized from ether-n-hexane to give 9.8 g of the titled compound as a colorless needles. mp. 134°–136° C.

IR Spectrum $\nu_{max}$nujol: 3350, 3250, 1760, 1740, 1710, 1690 cm⁻¹.

NMR Spectrum (CDCl₃, 60 MHz) δ: 2.30 & 2.33(each s,CH₃), 3.1–3.3

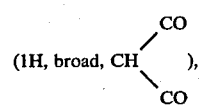

(1H, broad, CH(CO)(CO)), 4.10(d,J=2 Hz,4—H), 4.50(q,J=2 & 9 Hz,3—H), 5.10(s,OCH₂), 7.30 (s,aromatic H₅), 7.50(d,J=9 Hz,NH), 7.90(s,NH).

EXAMPLE 33

[3R,4R]-3-Benzyloxycarbonylamino-4-(1-t-butoxycarbonyl-1-methoxycarbonyl)methyl-2-oxoazetidine A solution of 2.8 mMol of methyl [3R,4R]-2-(3-benzyloxycarbonylamino-4-chloro-2-oxoazetidin-1-yl)-2-oxoacetate in 10 ml of dichloromethane, which is prepared by the procedure described in example 32, is stirred at −78° C., thereto is added a solution consisting of 0.5 ml of t-butyl acetoacetate and 2.8 ml of 1 M methanolic lithium methoxide. After the mixture is stirred for 30 min., 1 ml of acetic acid is added to the reaction solution. The solution is shaken with 150 ml of ethyl acetate and 30 ml of a saturated aqueous solution of sodium chloride. The separated organic layer is dried over magnesium sulfate, followed by concentration. The residue is subjected to flash column chromatography [silica gel, 30 g (Art 9385 Silica-gel 60, Mesh 230–400, Merck, Germany)] and developed with ethyl acetate-n-hexane (1:1) as eluent. The fractions containing the desired compound are collected and evaporated to afford 433 mg of the titled compound as colorless solid.

Thin Layer Chromatography: Rf=0.33 (Merck TLC plate 60 $F_{254}$, AcOEt-n-hexane=1:1)

IR Spectrum $\nu_{max}$(KBr): 3320, 2980, 1770, 1710, 1530, 1455, 1370, 1260, 1145, 1055 840, 780, 740, 700 $cm^{-1}$.

NMR Spectrum (CDCl$_3$, 60 MHz) δ: 1.38 & 1.40(each s,C(CH$_3$)$_3$), 2.20(s,CH$_3$CO), 3.67(d,J=9 Hz, —COCHCO—), 3.5–4.5(m,4—H), 5.56(dd,J=2 & 8 Hz, 3—H), 6.29 & 6.25(each d,J=8 Hz,3—NH), 6.85(s,NH), 7.19(s,aromatic H$_5$).

What we claim is:

1. A compound of the formula:

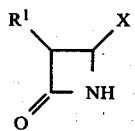

wherein $R^1$ represents phthalimido, benzyloxycarbonylamino, halogen or straight-chain, branched or cyclic alkyl of one to eight carbon atoms which has a hydroxy substituent; X represents (1) a group of the formula,

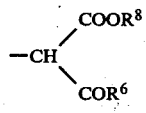

wherein $R^8$ is a carboxyl-protecting group, and $R^6$ is lower alkyl of one to four carbon atoms, halogenomethyl, methylthiomethyl, phenylthiomethyl, naphthylthiomethyl, carboxymethyl whose carboxyl may be protected, lower alkoxy of one to four carbon atoms, halogeno lower alkoxy of one to four carbon atoms, benzyloxy, p-nitrobenzyloxy, o-nitrobenzyloxy, lower alkylthio of one to four carbon atoms, amino lower alkylthio of one to four carbon atoms whose amino group may be protected, or amino lower alkenylthio of two to four carbon atoms whose amino group may be protected; or (2) a group of the formula,

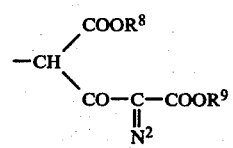

wherein $R^8$ and $R^9$ respectively represent a carboxyl-protecting group.

2. A compound as claimed in claim 1, wherein the carboxy-protecting group as defined in $R^6$, $R^8$ and $R^9$ is methyl, 2,2,2-trichloroethyl, tertiaryl alkyl of four to six carbon atoms, alkanoylmethyl of one to six carbon atoms, N-phthalimidomethyl, benzoylmethyl, benzyl, p-bromobenzyl, p-nitrobenzyl, p-methoxybenzyl, benzhydryl, trityl, phenyl, naphthyl, trimethylsilyl or triethylsilyl.

3. A compound as claimed in claim 1, wherein the amino-protecting group is a monovalent protective group selected from t-butoxycarbonyl, trichloroethoxycarbonyl, benzyloxycarbonyl, p-methoxybenzyloxycarbonyl, p-nitrobenzyloxycarbonyl, isobornyloxycarbonyl and trityl; or a divalent protective group selected from phthaloyl, succinyl and maleyl.

4. A compound as claimed in claim 1, wherein $R^1$ represents phthalimido, benzyloxycarbonylamino or straight-chain, branched or cyclic alkyl of 1 to 8 carbon atoms which has a hydroxy substituent.

5. A compound as claimed in claim 1, namely 4-[1-t-butoxycarbonyl-3-diazo-2-oxo-3-(2,2,2-trichloroethoxycarbonyl)propyl]-3-(1-hydroxyisopropyl)-2-oxoazetidine.

6. A compound as claimed in claim 1, namely 3-benzyloxycarbonylamino-4-(1-chloroacetyl-1-ethoxycarbonyl)-methyl-2-oxoazetidine.

7. A compound as claimed in claim 1, namely 4-(1-acetyl-1-t-butoxycarbonyl)methyl-3-phthalimido-2-oxoazetidine.

8. A compound as claimed in claim 1, namely 4-(1-acetyl-1-t-butoxycarbonyl)methyl-3-benzyloxycarbonylamino-2-oxoazetidine.

9. A compound as claimed in claim 1, namely 4-(1-t-butoxycarbonyl-1-chloroacetyl)methyl-3-phthalimido-2-oxoazetidine.

* * * * *